United States Patent [19]

Cuine et al.

[11] Patent Number: 5,431,902
[45] Date of Patent: Jul. 11, 1995

[54] NEW MEDICAMENT AEROSOL FORMULATION BASED ON FUSAFUNGINE

[75] Inventors: Alain Cuine, Saint Jean de Braye; Serge Morisseau, Saban, both of France

[73] Assignee: Adir et Compagnie, Courbevoie, France

[21] Appl. No.: 241,807

[22] Filed: May 12, 1994

[30] Foreign Application Priority Data

May 25, 1993 [FR] France ................. 93 06179

[51] Int. Cl.⁶ .................... A61K 9/12; A61K 7/48
[52] U.S. Cl. ................................... 424/45
[58] Field of Search ............................ 424/45

[56] References Cited

U.S. PATENT DOCUMENTS

| | | | |
|---|---|---|---|
| 3,305,445 | 2/1967 | Servier | 167/58 |
| 5,073,206 | 12/1991 | Wilson et al. | 134/40 |
| 5,225,183 | 7/1993 | Purewal et al. | 424/45 |

OTHER PUBLICATIONS

Haler (I) J. Int. Med. Res. 5(1): 61–64 (1977) CA. 87:16430.
Haler (II) Vie Med. 61(6): 507–508 (1980) CA. 93:38241.
Nolibe et al Mal. Med./Drugs Dis. 3(1): 37–42 (1987) CA. 107:32813.
Biofarmasa (Servier) Derwent Abstr. of U.S. 3305445 (Feb. 1967).
Riker Lab Inc (Green Leaf/Purental Derwent C.A. 114: 6906 Abstr. of U.S. 5225/83, E.P. 372777 & E.P. 499344.
Schultz et al (MMM) Derwent Abstr. of WO/PCT92/06675 (Apr. 30, 1992) CA. 116:262566.
Moris et al (MMM) Derwent Abstr. of WO/PCT92/22286 (Dec. 23, 1992) CA. 118:87671.
Oschmann Derwent Abstr. of Ger DE 4123663 (Jan. 21, 1993).
Bonnacker et al CA. 117:258216 of Ger DE 4038203 (Jun. 4, 1992).
Yoshira et al CA. 116:196649 of JPN 03 285997 (Dec. 17, 1992).
Purewal et al CA. 114:171307 of WO/PCT 9007333 (Jul. 12, 1990).

*Primary Examiner*—Shep K. Rose
*Attorney, Agent, or Firm*—Gordon W. Hueschen

[57] ABSTRACT

New medicament aerosol formulation based on fusafungine comprising excipient which is either dimethyl isosorbide or preferably, isopropyl myristate, and using as propellant 1,1,1,2-tetrafluoroethane.

10 Claims, No Drawings

NEW MEDICAMENT AEROSOL FORMULATION BASED ON FUSAFUNGINE

The present invention relates to a new pharmaceutical aerosol based on fusafungine, to a process for its preparation and to its use for therapeutic purposes.

Fusafungine is an antibiotic which is locally active against numerous phyla including: group A streptococci, pneumococci, staphylococci, certain strains of neisseria, certain anaerobic germs, candida and mycoplasma pneumoniae.

Fusafungine also exhibits anti-inflammatory properties.

Those types of properties makes fusafungine especially valuable for use in the local treatment of inflammations and of infections of the mucosa of the oropharynx and of the airways during the course of sinusitis, rhinitis, rhinopharyngitis, tonsillitis, the sequelae of a tonsillectomy, laryngitis, tracheitis, bronchitis . . . .

For indications in which it is useful to the patient, fusafungine is essentially administered by the oral or nasal route.

More especially, for about thirty years fusafungine has been presented—both to the medical profession and to the public—in the form of an aerosol of which the formulation comprises, as well as the active ingredient, a mixture of the following excipients: saccharin, compounded oil, orange flower oil, ethanol, benzododecinium bromide and isopropyl myristate. That composition contains in addition a propellant, dichlorodifluoromethane.

That pharmaceutical formulation, currently on the market, has the particularly advantageous characteristic of being a solution of the active ingredient in a mixture of excipients having a dissolving ability, consisting of ethanol, orange flower oil, compounded oil, isopropyl myristate and benzododecinium bromide. That characteristic, not very common for an aerosol, enables the aerosol particles administered to reach all of the respiratory passageways, including the pulmonary alveoli, ensuring maximum therapeutic efficacy.

A further advantage, also resulting from the fact that the aerosol is a solution, is that the preparation of such a formulation is easy : the phenomena of separation of the constituents, flocculation, sedimentation, lack of homogeneity, met in the case of suspensions, do not occur.

However, for the manufacturer who is charged with the manufacture and then the sale of that specialty, such a formulation has the disadvantage that it includes, as well as the active ingredient, seven separate excipients that are necessary to obtain a composition having the characteristics required for the preservation of and for the administration to humans of a pharmaceutical specialty.

It is easy to imagine the problems a manufacturer may encounter in the use of seven excipients for a formulation that contains only one active ingredient. All that is required is an interruption in supply on the part of one of the suppliers of the excipients and the manufacturer is no longer able to manufacture the pharmaceutical composition. Because of its indications, the requirement of that specialty is largely seasonal. It is easily conceivable that an interruption in supply, even for a short period, of only one of those excipients might have significant consequences:

for the manufacturer, a loss in sales equivalent to one year's production of one of his more important specialties (in number of units sold), for numerous patients, the impossibility of finding a very effective and well tolerated medicament.

It was in the light of the above that research was carried out with the aim of reducing the number of components of that formulation based on fusafungine, while at the same time retaining the qualities inherent in a pharmaceutical composition in aerosol form.

Surprisingly, it appeared that replacement of propellant 12 by propellant 134a, also called 1,1,1,2-tetrafluoroethane, made it possible to reduce to one only the number of excipients indispensable for a formulation based on fusafungine presented in aerosol form.

The pharmaceutical composition is accordingly reduced to the following three constituents:

the active ingredient, in this case fusafungine, the propellant, indispensable for any aerosol, in this case propellant 134a, one other excipient only, either dimethyl isosorbide or, preferably, isopropyl myristate.

First of all, one of the main advantages of the previous formulation currently on the market has been retained: a solution is always obtained despite the removal of several excipients having a dissolving ability, and that is surprising having regard to the physicochemical characteristics of fusafungine. The maximum therapeutic efficacy and the ease of manufacture of the pharmaceutical specialty have been retained.

Another advantage of the present invention is that the pharmaceutical composition obtained by using propellant 134a can be variable as a function of the supplies of starting materials. In particular if, in the pharmaceutical composition currently marketed which contains seven excipients, the propellant 12 is replaced by propellant 134a, a new composition is obtained which also exhibits the characteristics of stability required for a pharmaceutical composition, in the same way as the composition containing as the only excipients propellant 134a and isopropyl myristate or dimethyl isosorbide. Conclusive tests have also been carried out by omitting one or several of the following other excipients : ethanol, benzododecinium bromide, eucalyptol, orange flower oil.

Generally, the new pharmaceutical composition may be presented in cans of a size ranging from 5 to 200 ml. The active ingredient, fusafungine, is present in an amount of from 0.01 to 5% by weight of the formulation according to the invention. The propellant is contained in the composition of the formulations according to the invention in an amount of between 55 and 95% by weight, preferably between 70 and 80% by weight, of the formulation. Fusafungine is incorporated with an excipient which is either dimethyl isosorbide or, preferably, isopropyl myristate, which excipient is present in the composition in an amount of between 10 and 40% by weight, preferably between 20 and 30% by weight.

The excipients found in the previous formulation can always be added:

| | |
|---|---|
| Saccharin | 0 to 1% by weight |
| Ethanol | 0 to 5% by weight |
| Benzododecinium bromide | 0 to 0.1% by weight |
| Orange flower oil | 0 to 2% by weight |
| Eucalyptol | 0 to 2% by weight |
| Aromatic compositions | 0 to 5% by weight |

The following Examples indicate particular embodiments of the invention and do not limit the invention in any way.

EXAMPLE 1:

Fusafungine: 50 mg
Isopropyl myristate quantity sufficient for: 5 ml
Propellant 134a: 15 ml.

EXAMPLE 2:

Fusafungine: 50 mg
Ethanol: 0.3 ml
Saccharin: 1.25 mg
80% solution of benzododecinium bromide: 2.5 mg
Compounded oil: 150 mg
Orange flower oil: 50 mg
Isopropyl myristate quantity sufficient for: 5 ml
Propellant 134a: 15 ml.

EXAMPLE 3:

Fusafungine: 50 mg
Saccharin: 1.25 mg
80% solution of benzododecinium bromide: 2.5 mg
Compounded oil: 150 mg
Orange flower oil: 50 mg
Isopropyl myristate quantity sufficient for: 5 ml
Propellant 134a: 15 ml.

EXAMPLE 4

Fusafungine: 25 mg
Ethanol: 50 ml
Saccharin: 5 mg
Eucalyptol: 25 mg
Compounded oil: 50 mg
Isopropyl myristate quantity sufficient for: 2.5 ml
Propellant 134a: 7.5 ml.

EXAMPLE 5

Fusafungine: 25 mg
Saccharin: 5 mg
Eucalyptol: 25 mg
Compounded oil: 50 mg
Isopropy myristate quantity sufficient for: 2.5 ml
Propellant 134a: 7.5 ml.

EXAMPLE 6

Fusafungine: 50 mg
Ethanol: 0.3 ml
Saccharin: 1.25 mg
Compounded oil: 150 mg
Orange flower oil: 50 mg
Isopropyl myristate quantity sufficient for: 5 ml
Propellant 134a: 15 ml.

EXAMPLE 7

Fusafungine: 25 mg
Saccharin: 5 mg
Isopropyl myristate quantity sufficient for: 2.5 ml
Propellant 134a: 7.5 ml.

EXAMPLE 8

Fusafungine: 50 mg
Ethanol: 100 ml
Saccharin: 10 mg
80% solution of benzododecinium bromide: 2.5 mg
Eucalyptol: 50 mg
Compounded oil: 100 mg
Isopropyl myristate quantity sufficient for: 5 ml
Propellant 134a: 15 ml.

EXAMPLE 9

Fusafungine: 50 mg
Saccharin: 1.25 mg
Compounded oil: 150 mg
isopropyl myristate quantity sufficient for: 5 ml
Propellant 134a: 15 ml.

EXAMPLE 10

Fusafungine: 50 mg
Ethanol: 0.3 ml
Saccharin: 1.25 mg
Compounded oil: 200 mg
isopropyl myristate quantity sufficient for: 5 ml
Propellant 134a: 15 ml.

EXAMPLE 11

Fusafungine: 50 mg
Saccharin: 1.25 mg
Compounded oil: 200 mg
Isopropyl myristate quantity sufficient for: 5 ml
Propellant 134a: 15 ml.

EXAMPLE 12

Fusafungine: 50 mg
Compounded oil: 200 mg
Isopropyl myristate quantity sufficient for: 5 ml
Propellant 134a: 15 ml.

EXAMPLE 13

Fusafungine: 50 mg
Dimethyl isosorbide: quantity sufficient for 5 ml
Propellant 134a: 15 ml.

In the formulations according to Examples 6, 8 and 10, the ethanol could be omitted without any drawback. In the formulations according to Examples 2.3 and 8, similarly the 80% solution of benzododecinium bromide could be omitted without any drawback.

The above formulations are prepared by mixing and stirring the various constituents. The required amount of the mixture is introduced into a suitable flask and an aerosol dose dispensing valve is inserted. The propellant 134a is introduced under pressure.

We claim:

1. Pharmaceutical composition in aerosol form consisting essentially of fusafungine as active ingredient, an excipient selected from isopropyl myristate and dimethyl isosorbide and, as propellant, 1,1,1,2-tetrafluoroethane (propellant 134a), the fusafungine being present in an amount between 0.01 and 5% of the total weight of the formulation, the 1,1,1,2-tetrafluoroethane being present in an amount between 55 and 95% of the total weight of the formulation, and the excipient being present in an amount between 10 and 40% of the total weight of the formulation.

2. Pharmaceutical composition according to claim 1 in which the excipient is isopropyl myristate.

3. Pharmaceutical composition according to claim 2 which consists essentially of:

Fusafungine: 50 mg
Isopropyl myristate quantity sufficient for: 5 ml
Propellant 134a: 15 ml.

4. Pharmaceutical composition according to claim 1 in which the excipient is dimethyl isosorbide.

5. Pharmaceutical composition according to claim 4 which consists essentially of:

Fusafungine: 50 mg

Dimethyl isosorbide quantity sufficient for: 5 Ml
Propellant 134a: 15 ml.

6. Pharmaceutical specialty intended for the administration of fusafungine to a patient by the oral or nasal route, comprising an aerosol container fitted with a dose dispensing valve, the aerosol container containing a pharmaceutical composition according to claim 1.

7. A process for the preparation of a pharmaceutical specialty which comprises filling an aerosol container with a pharmaceutical composition according to claim 1 and fitting the aerosol container with a dose dispensing valve.

8. Method of locally treating inflammation and infection of the mocosa of the oropharynx and of the airways during the course of sinusitis, rhinitis, rhinopharyngitis, tonsillitis, the sequelae of a tonsillectomy, laryngitis, tracheitis and bronchitis, comprising the step of orally or nasally administering a pharmaceutical specialty according to claim 6.

9. Pharmaceutical composition according to claim 2 wherein the isopropyl myristate is present in an amount between 20 and 30% of the total weight of the formulation.

10. Pharmaceutical composition according to claim 4 wherein the dimethyl isosorbide is present in an amount between 20 and 30% of the total weight of the formulation.

* * * * *

UNITED STATES PATENT AND TRADEMARK OFFICE
CERTIFICATE OF CORRECTION

PATENT NO. : 5,431,902
DATED : Jul. 11, 1995
INVENTOR(S) : Alain Cuine, Serge Morisseau Page 1 of 2

It is certified that error appears in the above-indentified patent and that said Letters Patent is hereby corrected as shown below:

TITLE PAGE, [57] ABSTRACT, line 3: "comprising" should read -- comprising an --.

Column 2, line 43: Add -- : --(colon) to end of line.

Column 2, line 44: Delete ":" from beginning of the line.

Column 2, line 47: "200 mi," should read -- 200 ml, --.

Column 3, line 43: "Isopropy" should read -- Isopropyl --.

UNITED STATES PATENT AND TRADEMARK OFFICE
CERTIFICATE OF CORRECTION

PATENT NO. : 5,431,902
DATED : Jul. 11, 1995
INVENTOR(S) : Alain Cuine, Serge Morisseau It is certified that error appears in the above-indentified patent and that said Letters Patent is hereby corrected as shown below:

Column 4, line 7: "isopropyl" should read
-- Isopropyl --.

Column 4, line 15: "isopropyl" should read
-- Isopropyl --.

Column 4, line 37: "Examples 2.3 and 8, should read: -- Examples 2, 3 and 8, --.

Signed and Sealed this

Thirtieth Day of April, 1996

Attest:

BRUCE LEHMAN

*Attesting Officer*        *Commissioner of Patents and Trademarks*